United States Patent
Kim

(10) Patent No.: US 9,265,480 B2
(45) Date of Patent: Feb. 23, 2016

(54) CEREBROVASCULAR ANALYZER

(75) Inventor: Kwang Tae Kim, Seoul (KR)

(73) Assignee: Seog San Hyeon (CN)

( * ) Notice: Subject to any disclaimer, the term of this patent is extended or adjusted under 35 U.S.C. 154(b) by 673 days.

(21) Appl. No.: 13/121,806

(22) PCT Filed: Oct. 1, 2009

(86) PCT No.: PCT/KR2009/005626
§ 371 (c)(1),
(2), (4) Date: Mar. 30, 2011

(87) PCT Pub. No.: WO2010/038994
PCT Pub. Date: Apr. 8, 2010

(65) Prior Publication Data
US 2011/0275909 A1      Nov. 10, 2011

(30) Foreign Application Priority Data

Oct. 2, 2008 (KR) .................. 10-2008-0096949

(51) Int. Cl.
| A61B 5/02 | (2006.01) |
| A61B 8/08 | (2006.01) |
| A61B 5/022 | (2006.01) |
| A61B 8/06 | (2006.01) |
| A61B 5/026 | (2006.01) |
| A61B 5/0402 | (2006.01) |
| A61B 7/04 | (2006.01) |

(52) U.S. Cl.
CPC . *A61B 8/08* (2013.01); *A61B 5/022* (2013.01); *A61B 5/02007* (2013.01); *A61B 8/06* (2013.01); *A61B 8/0816* (2013.01); *A61B 5/026* (2013.01); *A61B 5/0402* (2013.01); *A61B 7/04* (2013.01); *A61B 8/485* (2013.01)

(58) Field of Classification Search
CPC .... A61B 5/02007; A61B 5/022; A61B 5/026; A61B 5/0402
USPC .................. 600/437, 483, 504, 509, 528
See application file for complete search history.

(56) References Cited

U.S. PATENT DOCUMENTS 4,703,758 A * 11/1987 Omura ................ 600/485
7,572,217 B1 * 8/2009 Koenig et al. ............ 600/16
(Continued)

FOREIGN PATENT DOCUMENTS

| KR | 10-0579936 | 5/2006 |
| KR | 10-2006-0078207 | 7/2006 |

(Continued)

*Primary Examiner* — Etsub Berhanu
*Assistant Examiner* — Karen Toth
(74) *Attorney, Agent, or Firm* — Gerald E. Hespos; Michael J. Porco; Matthew T. Hespos

(57) ABSTRACT

The present invention relates to a cerebrovascular analysis system which enables early diagnosis of various incurable cerebrovascular diseases such as cerebral thrombosis by measuring an elastic coefficient, blood vessel compliance, blood flow resistance, and blood flow in each cerebrovascular branch. The measurement is achieved by biomechanically analyzing blood vessels in the brain using an electrocardiogram, phonocardiogram, electroencephalogram, pulse wave, and ultrasonic doppler signal as basic data in order to measure biomechanical properties and blood flow properties of blood vessels in the brain for the diagnosis of cerebrovascular diseases.

6 Claims, 5 Drawing Sheets

(56) References Cited

U.S. PATENT DOCUMENTS

| | | | |
|---|---|---|---|
| 2002/0082514 A1* | 6/2002 | Williams et al. | 600/544 |
| 2003/0109772 A1* | 6/2003 | Mills | 600/310 |
| 2007/0124867 A1* | 6/2007 | Woods et al. | 7/164 |
| 2009/0124867 A1* | 5/2009 | Hirsh et al. | 600/301 |
| 2010/0204589 A1* | 8/2010 | Swoboda et al. | 600/485 |
| 2012/0059246 A1* | 3/2012 | Taylor | 600/419 |
| 2013/0204139 A1* | 8/2013 | Kashif et al. | 600/454 |

FOREIGN PATENT DOCUMENTS

| | | | | |
|---|---|---|---|---|
| KR | 10-2008-0048010 | | 5/2008 | |
| WO | WO 2009/014419 | * | 1/2009 | A61B 5/00 |

* cited by examiner

CEREBROVASCULAR ANALYZER

CROSS-REFERENCE TO RELATED APPLICATION

This application is a U.S. national stage application of International Application No. PCT/KR2009/005626 filed on Oct. 1, 2009, which claims priority to Korean Patent Application No. 10-2008-0096949 filed on Oct. 2, 2008, the entire contents of which are hereby incorporated by reference.

BACKGROUND OF THE INVENTION

1. Field of the Invention

The present invention relates to a cerebrovascular analysis system for analyzing the cerebrovascular diseases by measuring a biodynamic property and a blood flow property in a cerebral blood vessel, more specifically to a cerebrovascular analyzer for an early diagnosis of a cerebral thrombosis and other cerebrovascular refractory diseases by defining a cerebrovascular system as the blood vessel system organized with an internal carotid artery branch, an anterior cerebral blood vessel branch, a middle cerebral blood vessel branch, a posterior cerebral blood vessel branch, a vertebral artery branch and a basilar artery branch and then by analyzing each cerebrovascular branch of the cerebrovascular system to show a organic change of blood vessel by calculating a elastic coefficient of blood vessel and to show a blood flow property and organic and functional changes of the cerebrovascular system simultaneously by measuring a compliance of blood vessel, a resistance of blood flow and a volume of blood flow.

2. Description of the Related Art

In the today's clinics, an ultrasonic Doppler system is used to early diagnose the cerebrovascular diseases. However, the ultrasonic Doppler system has a limit to apply in clinics due to the incapability to measure the property of blood vessel.

Several cerebrovascular disease analyzers are developed until now such as angiography, MRA, FMRI, SPET, TCD, TEE, TTE, QFM and CVD.

The advantage of the angiography among them is that it is able to directly observe the progress of the diseases of blood vessel itself, but a blood vessel invasive operation is basically needed to inject a contrast medium and the operation is complex.

MRA and FMRI are the analyzing system to overcome the defects of the angiography, but they are only used in a certain ward due to the high cost of manufacture and diagnosis.

Especially, MRA, FMRI and SPET are used to identify a distribution of blood vessel, a blood flow property, a region of low blood flow, etc., although some differences are existed each other, but the property of blood vessel is not identified by them.

The ultrasonic quantitative flow measurement system (QFM) and the cerebrovascular property measurement system (CVD) enable to calculate the volume of blood flow of the carotid artery and the compliances of the middle cerebral artery and the anterior cerebral artery with low cost.

However, in order to assess the organic and functional states of blood vessel characterizing the blood vessel property, it is needed to know information of the elastic coefficient of blood vessel, the compliance of blood vessel and the resistance of blood flow, etc., for reflecting the organic and functional states of blood vessel itself rather than information related to the blood flow state such as a volume of blood flow in blood vessel and a blood pressure acted on the blood vessel wall.

However, it is a very difficult problem to measure the elastic coefficient of blood vessel, the compliance of blood vessel, a diameter of blood vessel, the resistance of blood flow and the volume of blood flow in each blood vessel branch of the cerebrovascular system for reflecting the organic state of blood vessel.

It is caused by the facts that the cerebovascular system has a complex structure and the biodynamic actions of blood vessel branches are different each other in the cerebrovascular system. It is also caused by a practical impossibility of the most accurate method that measures the elastic coefficient as an indicator of the organic change of blood vessel in human body by pulling a blood vessel sampled from living body with a tension apparatus.

In 2002, Werner G, Marifan C, Tonny M, Jeffrey C, etc., professors of California University in U.S.A, studied on biodynamic property of cerebral blood vessel of human and published a paper as Mechanical and Failure Properties of Human Cerebral Blood Vessels which is related to the property of the cerebral blood vessel.

However, because the blood vessels of human were sampled and tested, the results of the experiment can't be used as the indicators to diagnose.

Various researches on the indirect measurements of the volume of blood flow, the compliance, the elastic coefficient, the resistance of blood flow, etc. in the cerebrovascular system have been going on.

From 1997 to 2004, the measurements of the compliance and the resistance of cerebrovascular system had been suggested by many researchers such as Biedma, Haoliu, Cwako shin, etc. in U.S.A.

However, the above research results only contained the general facts on the blood pressure, the compliance, the elastic coefficient, the resistance and the distribution of blood flow in the cerebrovascular system, but did not obtain contents to apply the clinics directly.

In 2006, KF-3000 apparatus to apply to the clinics was developed by Ding Guanghong, a professor of Fudan University in Shanghai, China, to calculate the blood flow volume of each blood vessel branch in the cerebrovascular system.

KF-3000 brought to the innovative results to obtain the property of blood flow in the cerebrovascular system, but KF-3000 did not develop TCD to early diagnose the cerebrovascular diseases due to the intangibleness of the property of blood vessel.

Unlike the study of Dr. Ding Guanghong, COLLIN in Japan suggested a ultrasonic quantitative flow measurement system, QFM-2000X, to assess the property of blood flow and the property of blood vessel in cerebrovascular system for early diagnosing the cerebrovascular diseases and also CVD-1000, as a similar apparatus to QFM-2000X, based on a pending patent, an apparatus measuring parameter of cerebrovascular and method thereof.

The features of the ultrasonic quantitative flow measurement system (QFM) and the pending patent, an apparatus measuring parameter of cerebrovascular and method thereof, are organized to show a possibility to early diagnose the cerebrovascular diseases by calculating the volume of blood flow of the internal carotid artery, the compliances of the middle cerebral blood vessel and the anterior cerebral blood vessel with low cost.

However, the features of the ultrasonic quantitative flow measuring instrument (QFM) and the above pending patent could not identify separately the organic change and the functional change as two basic properties of blood vessel by selecting the compliance of blood vessel and the blood flow indicator as basic measurement indicators.

Especially, the ultrasonic quantitative flow measurement system (QFM-2000X) and the cerebrovascular property measurement system (CVD-1000) showed several defects to calculate the compliance and the resistance of the cerebrovascular system.

QFM-2000X calculated the compliance C and the resistance R to assess a left cerebrovascular system and a right cerebrovascular system under the assumption that the cerebrovascular system is divided to left and right and the blood flow volume of the cerebrovascular system is the volume of blood flow which flows into the internal carotid artery.

Therefore, it was not able to assess each blood vessel branch of brain.

Also, to obtain the compliance and the resistance of the cerebrovascular system, the features of them considered a blood pressure waveform as a pressure pulse waveform and a blood flow waveform as an ultrasonic waveform and calculated C and R by adjusting the waveforms to coincide with each other, but the results of C and R had defects that the amplitude of vibration was large and the approximation of curve was largely different from real phenomenon.

In fact, when the blood flow waveform is measured by the ultrasonic Doppler, the measurement error is very large due to the error of horizontal level. Therefore, the coincidence of two waveforms with the errors is not real and has very low reproducibility. Additionally, the approximation of curve vs. curve creates a big error by very little waveform change.

Therefore, the compliance C and the resistance R measured by QFM-2000X does not an enough mortgage to use as the clinical indicators because the values of C and R are differed 10-100 times from each examiner due to the irreproducibility.

The configuration of the pending patent, an apparatus measuring parameter of cerebrovascular and method thereof, could not find an accurate clinic indicator by assuming that when the cerebrovascular system is modeled and analyzed, the volume of blood flow which flows into the brain is equal to k times of the volume of cardiac output instead of calculating the volume of blood flow which flows into the brain.

The configuration of the pending patent, an apparatus measuring parameter of cerebrovascular and method thereof, is suggested as followings.

Although the cross-unital area of the internal carotid artery is reduced to 80-90%, the blood flow volume which flows into the internal carotid artery does not changed. Accordingly, the blood flow volume of the internal carotid artery can be calculated by an equation $Q_c = K_c S_v$, where, $S_v$ is a cardiac output and $K_c$ is a ratio coefficient.

However, the above assumption did not an enough mortgage as a medical diagnosis apparatus.

Also, the configuration of the pending patent, an apparatus measuring parameter of cerebrovascular and method thereof, reduced the correctness of disease diagnosis by assuming that the compliances and resistances of the anterior and posterior cerebral arteries were divided by a predetermined rate.

Specifically, QFM-2000X and the pending patent, an apparatus measuring parameter of cerebrovascular and method thereof, did not suggested a method to obtain the compliance and resistance of the posterior cerebral artery.

Accordingly, QFM-2000X and the pending patent, an apparatus measuring parameter of cerebrovascular and method thereof, did not obtained the elastic coefficient, but obtained the compliance and the resistance for assessing the property of the cerebrovascular system. However, the obtained compliance and resistance showed many defects.

Therefore, it is needed new solution to accurately calculate the elastic coefficient, the compliance, the resistance, and the volume of blood flow of each blood vessel branch in the cerebrovascular system.

SUMMARY OF THE INVENTION

The present invention is contrived for solving the above-mentioned problems of conventional technology. The objective of the present invention is to provide a cerebrovascular analyzer which enables to early diagnose various cerebrovascular refractory diseases as well as a cerebral thrombosis by analyzing the cerebrovascular system biodynamically on the basis of the basic data such as an electrocardiogram signal, a phonocardiogram signal, a plethysmogram signal, and an ultrasonic Doppler signal to obtain the biodynamic property and the blood flow property of the cerebrovascular blood vessel branches and by calculating the elastic coefficient, the compliance, the resistance, and the blood flow volume of each blood vessel branch in cerebrovascular system.

To achieve the above-mentioned objective, the present invention has the first feature that a cerebrovascular analyzer comprises: a bio-signal measurement system including a bio-signal measuring sensor unit which comprises an electrocardiogram (ECG) sensor, a phonocardiogram (PCG) sensor, an accelerated plethysmogram (APG) sensors and an ultrasonic sensor, and a bio-signal reception and process unit which is connected to each of the sensors of the bio-signal measuring sensor unit for receiving and processing bio-signals measured by the sensors; and an analysis indicator calculation system including a main processing unit which is connected to the bio-signal reception and process unit for communicating and calculating biodynamic indicators of a cerebrovascular system from the bio-signals, an input unit which is connected to the main processing unit for receiving control commends of user, and an output unit which is connected to the main processing unit for displaying the calculated results, wherein the main processing unit is programmed to calculate the biodynamic indicators from basic data including a cerebrovascular pressure curve synthesized with the bio-signals of the bio-signal measurement system, a systolic area and a diastolic area of the cerebrovascular pressure curve and an cerebrovascular blood flow volume.

The present invention has the second feature that the bio-signal reception and process unit comprises: a microcontroller which controls to process the bio-signals received from the bio-signal measuring unit and to transmit processed bio-signals to the main processing unit; a multi-signal selector which selects one of the bio-signals received from the ECG sensor, the PCG sensor, the APG sensors and the ultrasonic sensor by a control signal of the microcontroller; a noise eliminator and signal amplifier which eliminates noises and/or controls amplification degree of the bio-signal selected by the multi-signal sensor by a control signal of the microcontroller; a signal switcher which receives the bio-signals from the noise eliminator and signal amplifier and selects one of the bio-signals to meet the control commands of the input unit or of embedded program in the main processing unit by a control signal of the microcontroller; a sample holder which samples and holds the bio-signal selected by the signal switcher by a control signal of the microcontroller; and an A/D converter which converts a holding bio-signal of the sample holder to a digital bio-signal and sends to the microcontroller by a control signal of the microcontroller.

The present invention has the third feature that the APG sensor is a cuff pulse wave sensor, a carotid artery pulse wave sensor or a femoral artery pulse wave sensor, and the bio-signal measurement system is configured to obtain an ECG waveform, a PCG waveform and an APG waveform synchronously by the bio-signal measuring sensor unit.

The present invention has the fourth feature that the APG sensors is a cuff pulse wave sensor being a cuff sphygmomanometer equipped with a pressure sensor.

The present invention has the fifth feature that the cuff pulse wave sensor comprises a rubber hose which is connected to an air pouch of the cuff sphygmomanometer, a branch hose which is connected to the rubber tube, and an adaptor which is connected to an exit of the branch hose, and the adaptor is assembled to an opening part of a sensor having the same structure as the carotid artery pulse wave sensor or the femoral artery pulse wave sensor.

The present invention has the sixth feature that the main processing unit is programmed to carry out the steps of: (1) receiving basic information data from the input unit and receiving the bio-signals from the bio-signal measurement system; (2) analyzing waveforms from the bio-signals and obtaining the cerebrovascular pressure curve, the systolic area and the diastolic area of the cerebrovascular pressure curve and the cerebrovascular blood flow volume from the waveforms; and (3) calculating the biodynamic indicators including from the cerebrovascular pressure curve, the areas of the cerebrovascular pressure curve, the cerebrovascular blood flow volume and the basic information data and displaying the results of cerebrovascular analysis.

The present invention has the seventh feature that the cerebrovascular system comprises a left posterior cerebral artery and a right posterior cerebral artery; and, among the biodynamic indicators of step 3, the compliances $C_{p1}$ and $C_{p2}$ and the resistances $R_{p1}$ and $R_{p2}$ of the left and right posterior cerebral arteries are calculated by the predetermined equations.

The present invention has the eighth feature that the cerebrovascular system comprises a left anterior cerebral artery and a right anterior cerebral artery; and, among the biodynamic indicators of step 3, the compliances $C_{a1}$ and $C_{a2}$ and the resistances $R_{a1}$ and $R_{a2}$ of the left and right anterior cerebral arteries are calculated by another equations.

The present invention has the ninth feature that the cerebrovascular system comprises a left middle cerebral artery and a right middle cerebral artery; and, among the biodynamic indicators of step 3, the compliances $C_{m1}$ and $C_{m2}$ and the resistances $R_{m1}$ and $R_{m2}$ of the left and right middle cerebral arteries are calculated by another equations.

The present invention has the tenth feature that the main processing unit is programmed to control the output unit to display the cerebrovascular compliance C and the cerebrovascular resistance R calculated in step 3 as a dot on a Compliance-Resistance (C-R) chart.

The present invention enables to early diagnose the risk of cerebrovascular diseases by analyzing an elastic coefficient for observing the organic change of each cerebrovascular branch and by calculating a cerebrovascular blood flow volume, a cerebrovascular compliance, and a cerebrovascular resistance for observing blood flow properties of a cerebrovascular system and the organic and the functional changes of each cerebrovascular branch.

DETAILED DESCRIPTION OF THE PREFERRED EMBODIMENTS

The following reference numbers are used throughout the drawings: reference number 10 indicates a cuff sphygmomanometer, 11 indicates a cuff, 12 indicates an adhesive means (Velcro), 13 indicates an air pouch, 14, 17 and 18 indicate a rubber hose, 15 indicates an air valve, 16 indicates an air supply means, 20 indicates an adapter, 21 indicates a branch hose, 22 indicates an attachment part of branch hose, 24 indicates a cover, 26 indicates a projecting part for connecting to adapter, 30 indicates a pressure sensor, 31 indicates a vent hole, 32 indicates an opening part, 34 indicates a housing body, 36 indicates a sensing lead line, 40 indicates an anterior cerebral communicating artery, 41 indicates an anterior cerebral artery, 42 indicates an internal carotid artery, 43 indicates a middle cerebral artery, 44 indicates a posterior cerebral communicating artery, 45 indicates a posterior cerebral artery, 46 indicates a basilar artery, 47 indicates an anterior inferior cerebellar artery, 48 indicates a vertebral artery, and 49 a posterior inferior cerebellar artery.

A detailed description of preferred embodiments of the present invention is provided below with respect to accompanying drawings. Because the present invention can be embodied in various forms, the technical idea of the present invention has to be not limited to the drawings and the embodiments described herein.

Figure 1:
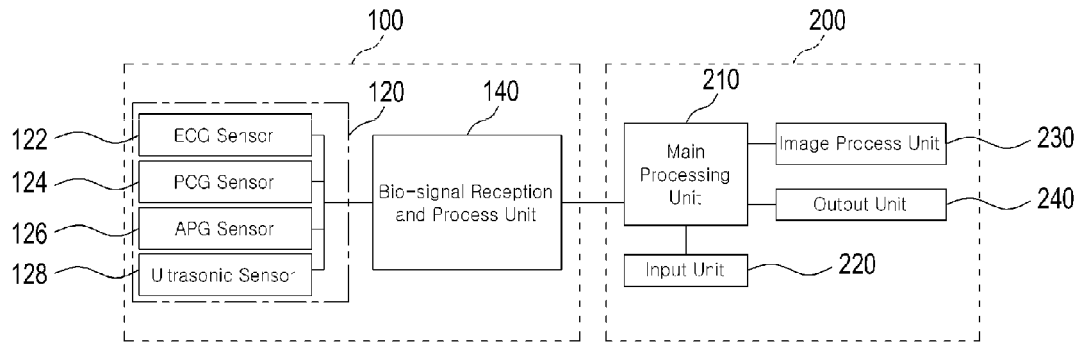
FIG. 1 is a block diagram of a cerebrovascular analyzer according to an exemplary embodiment of the present invention.
Figure 2:
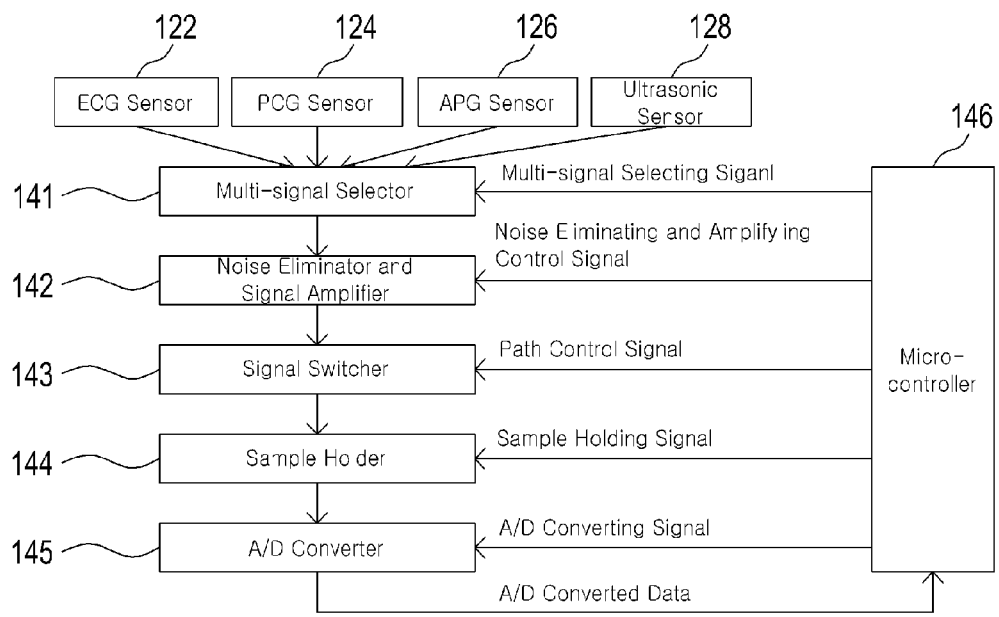
FIG. 2 is a block diagram conceptually showing the constitution and the signal flow of the bio-signal reception and process unit in FIG. 1.
Figure 3:
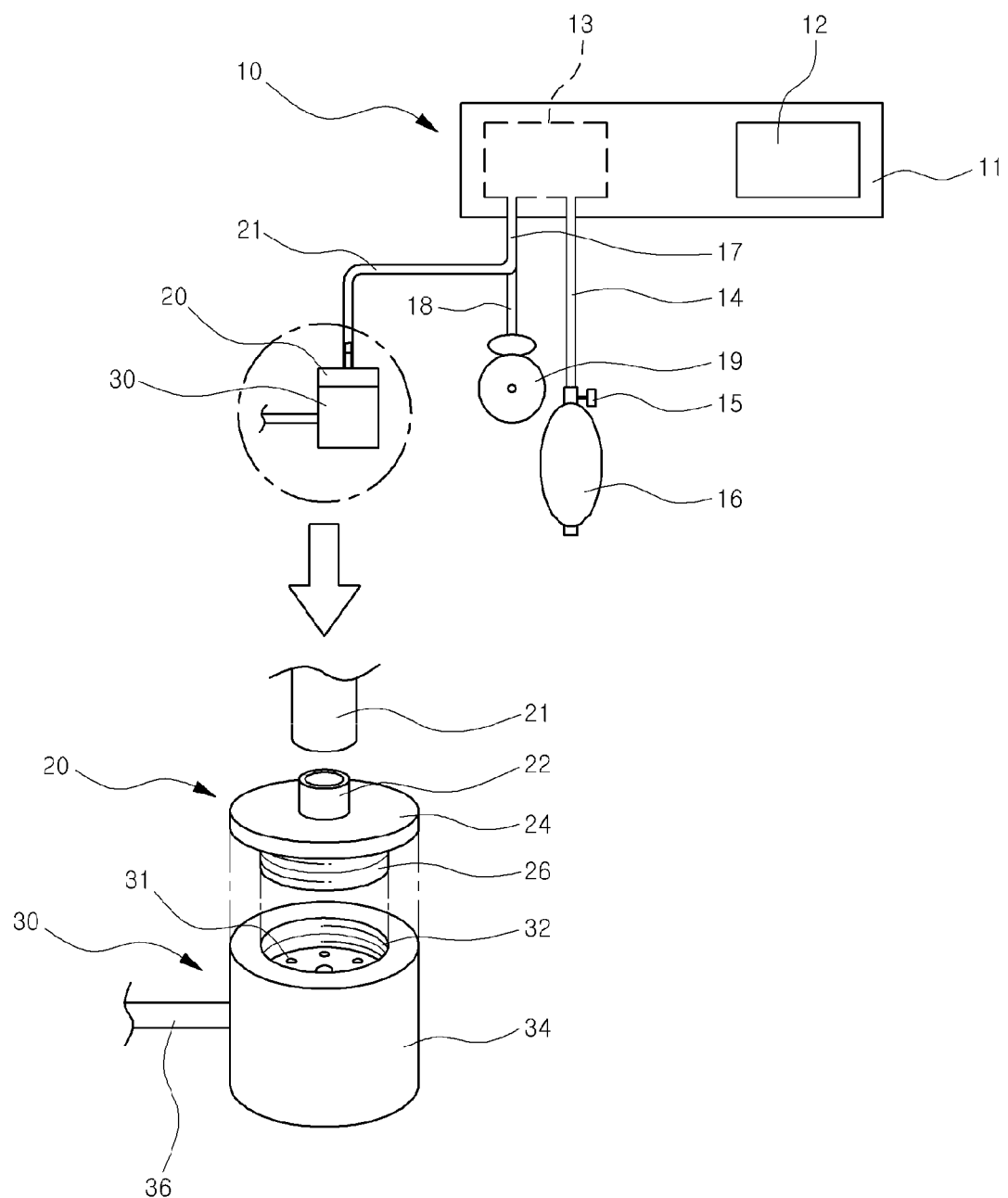
FIG. 3 is a front and disassembled perspective views of a cuff pulse wave sensor as the APG sensor showed in FIG. 1.
Figure 4:
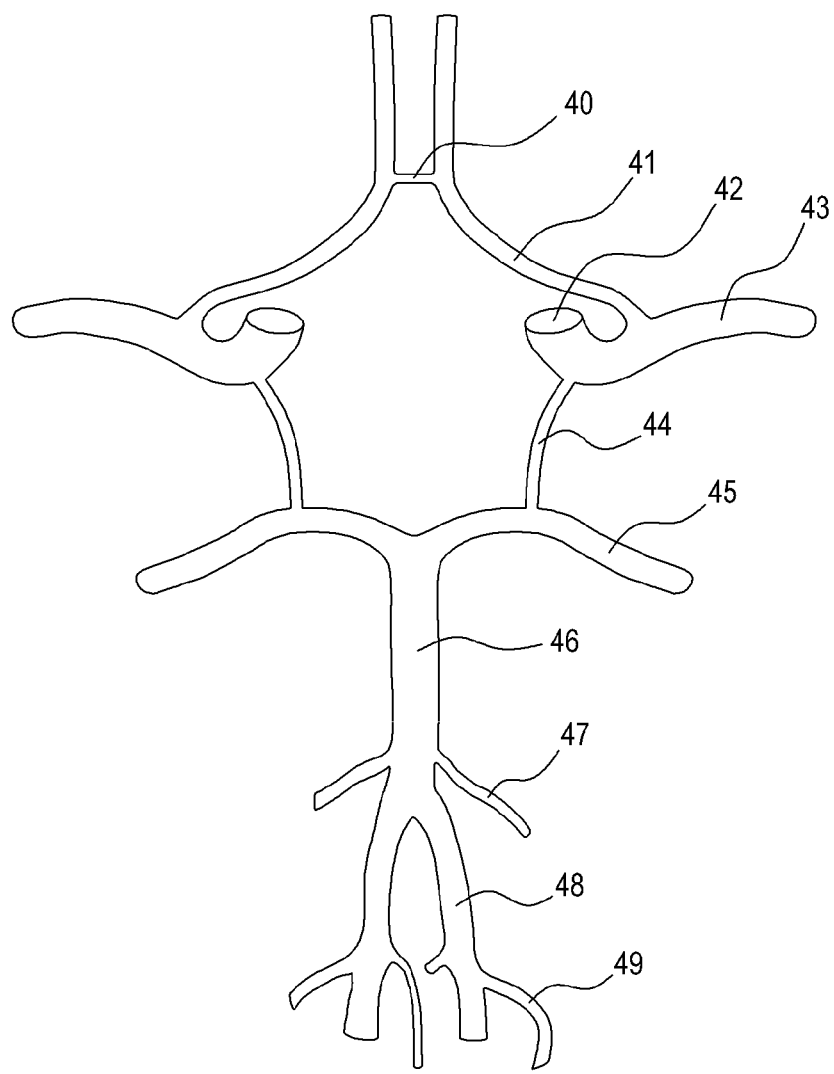
FIG. 4 is a conceptual diagram of the circle of Willi which shows a connection state of cerebrovascular branches.
Figure 5:
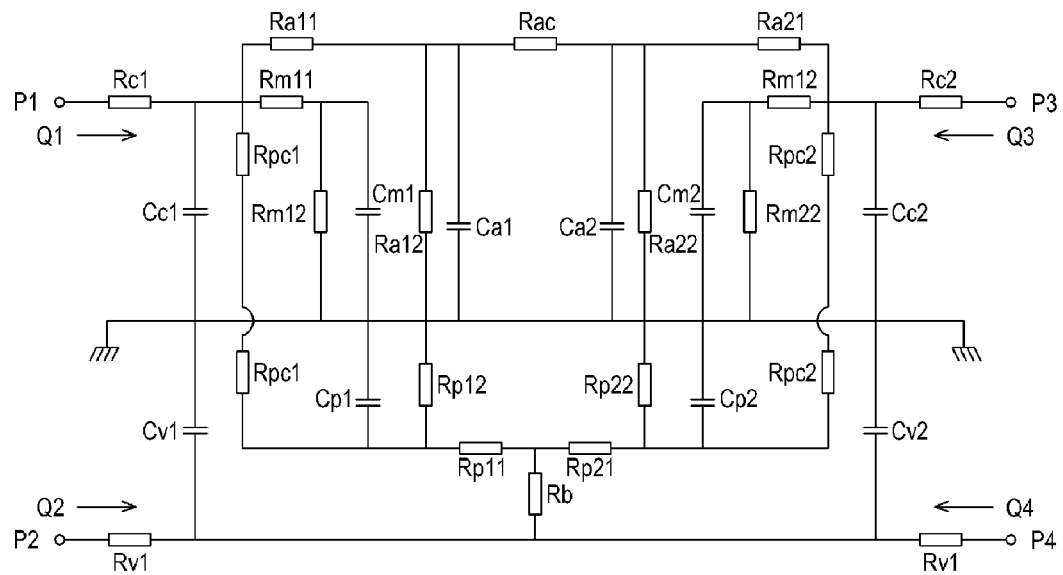
FIG. 5 is a circuit diagram of a cerebrovascular model of FIG. 4 which seems that an internal carotid artery branches to an anterior cerebral artery and a middle cerebral artery.
Figure 6:
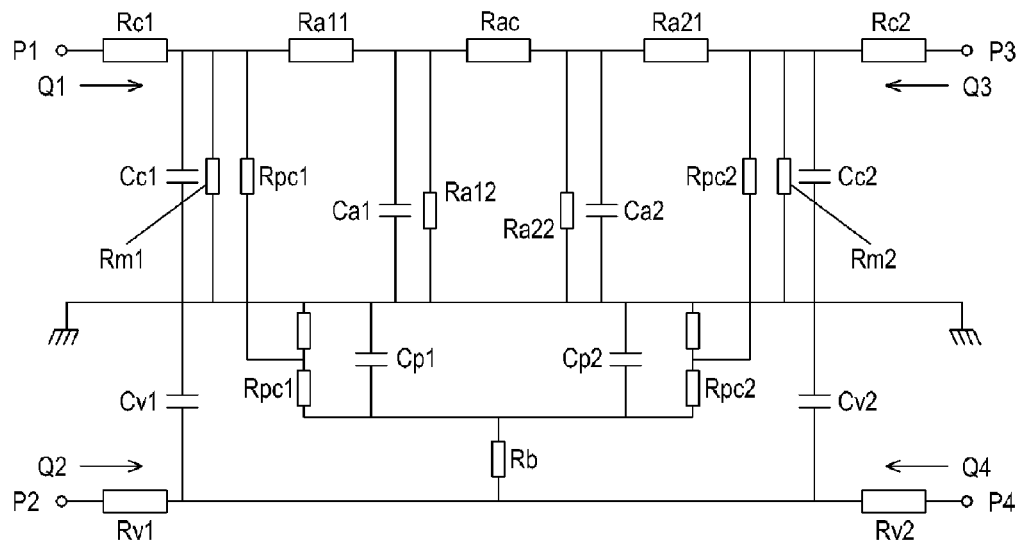
FIG. 6 is a circuit diagram of a cerebrovascular model of FIG. 4 which seems that an internal carotid artery connects to a middle cerebral artery as a single blood vessel branch.
Figure 7:
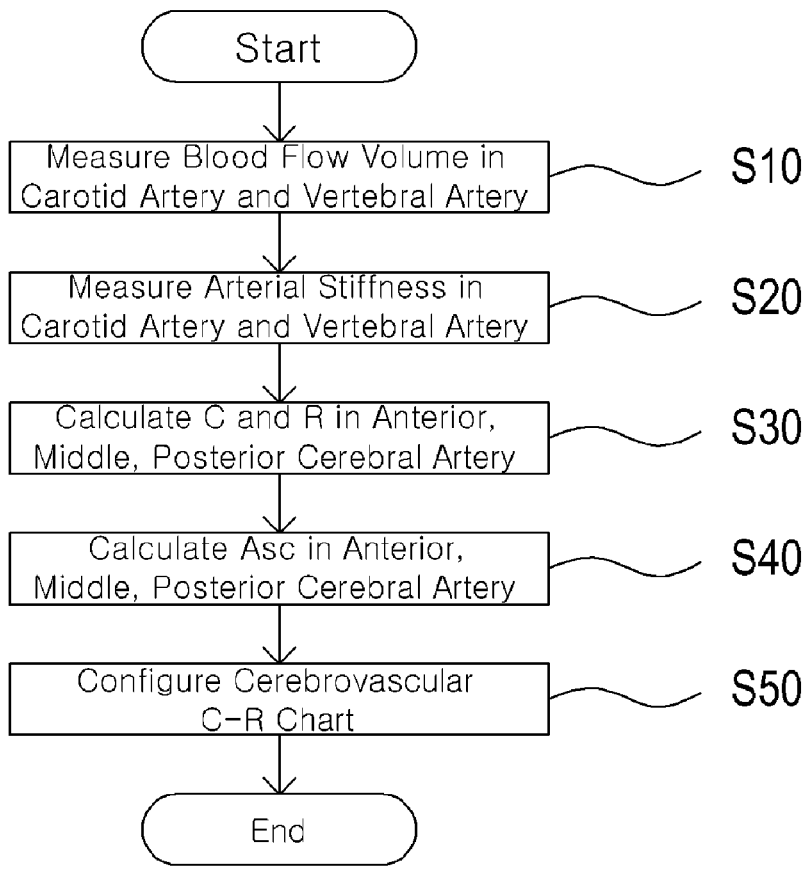
FIG. 7 is an operational diagram according to an exemplary embodiment of the main processing unit of FIG. 1.
Figure 8:
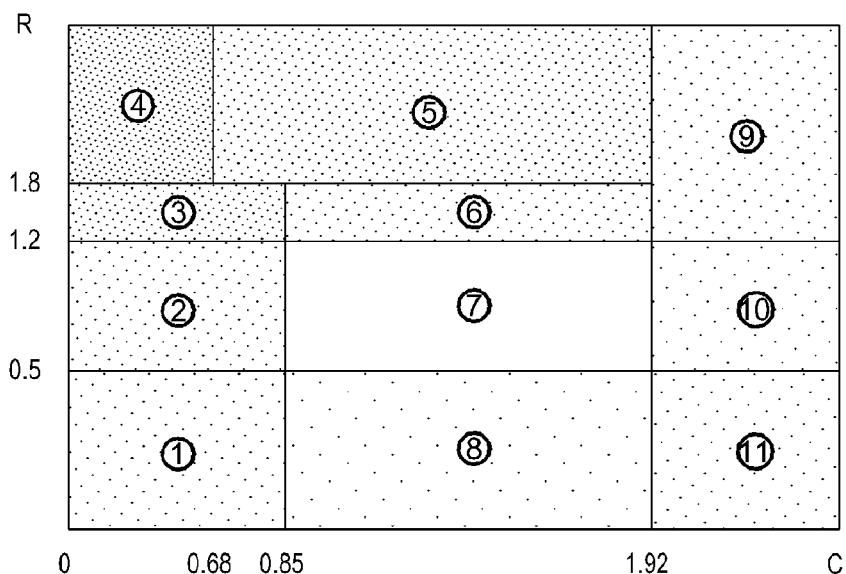
FIG. 8 is a diagram of the C-R chart displaying the analysis results of the main processing unit as an exemplary embodiment.

FIG. 1 is a block diagram of a cerebrovascular analyzer according to an exemplary embodiment of the present invention. FIG. 2 is a block diagram conceptually showing the constitution and the signal flow of the bio-signal reception and process unit in FIG. 1. FIG. 3 is a front and disassembled perspective views of a cuff pulse wave sensor as the APG sensor showed in FIG. 1. FIG. 4 is a conceptual diagram of the circle of Willi which shows a connection state of cerebrovascular branches. FIG. 5 is a circuit diagram of a cerebrovascular model of FIG. 4 which seems that an internal carotid artery branches to an anterior cerebral artery and a middle cerebral artery. FIG. 6 is a circuit diagram of a cerebrovascular model of FIG. 4 which seems that an internal carotid artery connects to a middle cerebral artery as a single blood vessel branch. FIG. 7 is an operational diagram according to an exemplary embodiment of the main processing unit of FIG. 1. And FIG. 8 is a diagram of the C-R chart displaying the analysis results of the main processing unit as an exemplary embodiment.

As shown in FIG. 1, a cardiovascular analyzer according to one embodiment of the present invention is characterized by basically comprising: a bio-signal measurement system including a bio-signal measuring sensor unit which comprises an electrocardiogram (ECG) sensor, a phonocardiogram (PCG) sensor, an accelerated plethysmogram (APG) sensor and an ultrasonic sensor, and a bio-signal reception and process unit which is connected to each of the sensors of the bio-signal measuring sensor unit for receiving and processing bio-signals measured by the sensors; and an analysis indicator calculation system including a main processing unit which is connected to the bio-signal reception and process unit for communicating and calculating biodynamic indicators of a cerebrovascular system from the bio-signals, an input unit which is connected to the main processing unit for receiving control commends of user, and an output unit which is connected to the main processing unit for displaying the calculated results, wherein the main processing unit calculates the biodynamic indicators from basic data including a cerebrovascular pressure curve synthesized with the bio-signals of the bio-signal measurement system, a systolic area and a diastolic area of the cerebrovascular pressure curve and an cerebrovascular blood flow volume.

Here, the ECG sensor 122 comprises at least three electrodes and is used to obtain an ECG waveform and to define the feature points (i.e., systolic upstroke point, systolic peak point, incisura point, diastolic peak point and diastolic end point) of the cerebrovascular pressure curve with the PCG sensor.

The PCG sensor 124 comprises a microphone to perceive the sound of open-and-shut of heart valves and is used to obtain a PCG waveform for defining the feature points of the cerebrovascular pressure curve.

The APG sensor 126 is used to obtain an APG waveform by sensing a pulse wave of the pulsatory motion. The APG sensor 126 comprises a pressure sensor having a piezoelectric element, but not limited to, or other device which senses the pulse wave.

In this embodiment, the APG sensor 126 is one of the sensors including a cuff pulse wave sensor to get information for a frequency spectrum of a cerebrovascular system, a carotid artery pulse wave sensor to get information for a probability density spectrum of the cerebrovascular system by directly measuring pulse waves of the left and right carotid arteries, and a femoral artery pulse sensor to get information for a pulse wave velocity (PWV) etc by directly measuring a pulse wave of the femoral artery.

Here, it is possible that the carotid artery pulse wave sensor and the femoral artery pulse wave sensor are the same kind of pressure sensor. The cuff pulse wave sensor is a cuff sphygmomanometer equipped with a pressure sensor.

As an embodiment, the detailed structure of the cuff pulse wave sensor is shown in FIG. 3. A branch hose 21 is connected to a rubber hose 14 or 17 which is connected to an air pouch 13 in the cuff sphygmomanometer 10. An adaptor 20 is connected to an exit of the branch hose 21 and is assembled to an opening part 32 of a sensor (e.g. a pressure sensor 30) having the same structure as the carotid artery pulse wave sensor or the femoral artery pulse wave sensor.

The ultrasonic sensor 128 is called as a trans-cranial Doppler (TCD) and is used to measure a cerebrovascular blood velocity and a cerebrovascular blood flow volume by the analysis of a reflective ultrasound wave detected by a probe placed on a cranial region where an ultrasound well transited.

As the above mentioned, the bio-signal measuring sensor unit 120 essentially comprises the ECG sensor 122, the PCG sensor 124, the APG sensor 126 and the ultrasonic sensor 128 for sensing the different bio-signals. The device embedded with the bio-signal reception and process unit 140 has at least four connectors for connecting to each of the sensors of the bio-signal measuring sensor unit 120.

Also, as shown in FIG. 2, the bio-signals reception and process unit 140 comprises: a microcontroller 146 which controls to process the bio-signals received from the bio-signal measuring unit 120 and to transmit processed bio-signals to the main processing unit 210; a multi-signal selector 141 which selects one of the bio-signals received from the ECG sensor 122, the PCG sensor 124, the APG sensor 126 and the ultrasonic sensor 128 by a control signal of the microcontroller 146; a noise eliminator and signal amplifier 142 which eliminates noises and/or controls amplification degree of the bio-signal selected by the multi-signal sensor 141 by a control signal of the microcontroller 146; a signal switcher 143 which receives the bio-signals from the noise eliminator and signal amplifier 142 and selects one of the bio-signals to meet the control commands of the input unit 220 or of embedded program in the main processing unit 210 by a control signal of the microcontroller 146; a sample holder 144 which samples and holds the bio-signal selected by the signal switcher 143 by a control signal of the microcontroller 146; and an A/D converter 145 which converts a holding bio-signal of the sample holder 144 to a digital bio-signal and sends to the microcontroller 146 by a control signal of the microcontroller 146.

Here, the multi-signal selector 141 is used to sequentially process the signals which are simultaneously measured and inputted by the ECG sensor 122, the PCG sensor 124, the APG sensor 126 and the ultrasonic sensor 128. The noise eliminator and signal amplifier 142 is used to make a standard waveform by filtering the noises of the obtained bio-signals and to control an amplification degree according to a patient (examinee).

As above mentioned, the bio-signal reception and process unit 140 is preferable to involve in the bio-signal measurement system 100 but, according to a circuit design, can be embedded in the main processing unit 210.

Next, the bio-signals obtained and processed by the bio-signal measurement system 100 is transferred to the analysis indicator calculator system 200 for synthesizing the cereborvascular pressure curve. The information including the area of the cereborvascular pressure curve, the blood flow volume and etc is used to calculate the biodynamic indicators.

As shown in FIG. 1, when the bio-signal reception and process unit 140 is separated from the main processing unit 210, a predetermined communicating means (e.g., RS-232C) is used to exchange the data between them.

The main processing unit 210 is a core unit, as like as a central processing unit (CPU) of computer, to process the measured data from the bio-signal reception and process unit 140 by the program saved in an internal memory part or an external memory part for calculating the biodynamic indicators which is used to analyze the cerebrovascular system.

Here, the biodynamic indicators for analysis of the cereborvascular system are the blood flow volume, the compliance, the blood flow resistance, the arterial stiffness and the blood flow velocity of each of the cerbrovascular branches.

First, the definition and the relationship of the biodynamic indicators used in this embodiment are simply described.

The blood flow volume is the volume of blood flowing in the cerbrovascular branch. The unit of blood flow volume is me, Q or Q(t) is used to express as a function of time, and S is used to express a blood volume having flowed for a time period (i.e., integral of Q for time). The blood flow volume is generally in direct proportion to the difference P-Pv of blood pressures and in inverse proportion to the blood flow resistance R between two sites longitudinally separated in the cerbrovascular branch. The small value of the blood flow volume causes the ischemic symptoms.

The compliance is a change of volume occurred at the unit volume of blood vessel forced by the unit force. The unit of compliance is d/mmHg and the compliance is simply written as C. The small value of C means the more stiffness or contraction of the blood vessel wall. On the contrary, the large value of C means the more flex or extending spasm occurs in the blood vessel wall.

The blood flow resistance means the resistance against the flow of blood in the cerbrovascular branch. The unit of blood flow resistance is mmHg/l, and is simply written as R. R is approximately determined by the rate of the difference P-Pv of the blood pressures and the blood flow volume Q between two sites longitudinally separated in the cerbrovascular branch.

The arterial stiffness Asc is an indicator showed how much power is needed to change the unit length of blood vessel and, in other words, showed the stiffness of blood vessel. The Asc reflects the organic change of blood vessel. The unit of Asc is $Kg/cm^2$ and Asc is generally proportional to the square of the propagation velocity of elastic wave.

Lastly, the blood flow velocity V is the speed of blood flowing in the cerbrovascular branch and is measured by the ultrasonic sensor 128 mainly. The unit of V is cm/s. The pulse wave velocity (PWV) reflects the elastic status of an aorta and is measured by the method recording pulse wave in the carotid artery and the femoral artery. The more stiffness of blood vessel wall is the more rapid of the velocity. Especially, the harder change of arteriosclerosis is the more rapid of the velocity of blood flow or the pulse wave velocity.

Also, in the words of the described biodynamic indicators, a subscript 'a' means an anterior cerebral artery 41, a subscript 'b' means a basilar artery 46, a subscript 'c' means an internal carotid artery 42, a subscript 'd' means the diastole of heart, a subscript 'm' means a middle cerebral artery 43, a subscript 'p' means a posterior cerebral artery 45, a subscript 's' means a systole of heart, a subscript 'v' means a vertebral artery 48, a subscript 'ac' means an anterior cerebral communicating artery 40, a subscript 'pc' means a posterior cerebral communicating artery 44, a subscript 'l' means a left, and a subscript 'r' means a right.

On the other hand, the main processing unit 210 is connected to the input unit 220 for receiving the control commands of user and to the output unit 240 for displaying the results calculated in the main processing unit 210.

Here, the output unit 240 comprises a screen output part through a monitor as well as a printer. Therefore, the image process unit 230 of FIG. 1 can be embedded in the screen output part.

Also, the input unit 220 comprises not only a keyboard and a mouse, but also a touch input means on the monitor of the screen output part.

In the above mentioned configuration, the core part is the calculation of the biodynamic indictors by some equations using the measurement and analysis of the bio-signals under the control of the main processing unit 210. Therefore, it is described in detail.

The control of the main processing unit 210 can be carried out by a program embedded in the main processing unit 210. The control program of the main processing unit 210 basically comprises the steps of: (1) receiving basic information data (e.g., a blood pressure, a height, a weight and a race of an examinee) from the input unit 220 and receiving the bio-signals from the bio-signal measurement system 100; (2) analyzing waveforms from the bio-signals and obtaining the cerebrovascular pressure curve, the systolic area and the diastolic area of the cerebrovascular pressure curve and the cerebrovascular blood flow volume from the waveforms; and (3) calculating the biodynamic indicators including a cerebrovascular compliance C and a cerebrovascular resistance R from the cerebrovascular pressure curve, the areas of the cerebrovascular pressure curve, the cerebrovascular blood flow volume and the basic information data and displaying the results of cerebrovascular analysis. The control of the main processing unit 210 can be variously carried out by the program as follows.

The above mentioned cerebrovascular system is called the cerebrovascular branches as shown in FIG. 4. According to one embodiment, the biodynamic indicators of each of the cerebrovascular branches including the left and right posterior cerebral arteries 45, the left and right anterior cerebral arteries 41 and the left and right middle cerebral arteries 43 are automatically calculated by predetermined equations and the results are displayed on the output unit 240 such as a C-R chart as shown in FIG. 8.

As described later, by the main processing unit 210, the biodynamic indicators of each of the cerebrovascular branches are calculated from cerebrovascular branch pressure curves $P_{a1}$, $P_{a2}$, $P_{c1}$, $P_{c2}$, $P_{p1}$, $P_{p2}$, $P_{v1}$, and $P_{v2}$ which are obtained by solving plural simultaneous equations made of the measured data $Q_{c1}$, $Q_{c2}$, $Q_{v1}$, and $Q_{v2}$.

For example, the compliances $C_{p1}$ and $C_{p2}$ and the resistances $R_{p1}$ and $R_{p2}$ of the left and right posterior cerebral arteries are calculated by Equations 1 to 4, respectively.

The compliance of the left posterior cerebral artery is $$C_{p1} = \frac{A_{p1s} - A_{p1d}}{P_{p1S} - P_{p1d}} \cdot \frac{S_{p1}}{A_{p1S} + A_{p1d}} \qquad \text{Equation 1}$$

The compliance of the right posterior cerebral artery is $$C_{p2} = \frac{A_{p2S} - A_{p2d}}{P_{p2S} - P_{p1d}} \cdot \frac{S_{p2}}{A_{p2S} + A_{p2d}} \qquad \text{Equation 2}$$

The resistance of the left posterior cerebral artery is $$R_{p1} = \frac{A_{p1S} + A_{p1d}}{S_{p1}} \qquad \text{Equation 3}$$

And the resistance of the right posterior cerebral artery is $$R_{p2} = \frac{A_{p1S} + A_{p1d}}{S_{p2}} \qquad \text{Equation 4}$$

In Equations 1 to 4, $P_{p1s}$ is a systolic blood pressure of the left posterior cerebral artery, $P_{p1d}$ is a diastolic blood pressure of the left posterior cerebral artery, $P_{p2s}$ is a systolic blood pressure of the right posterior cerebral artery, $P_{p2d}$ is a diastolic blood pressure of the right posterior cerebral artery, $A_{p1s}$ is an area of a systolic left posterior cerebral artery pressure curve, $A_{p1d}$ is an area of a diastolic left posterior cerebral artery pressure curve, $A_{p2s}$ is an area of a systolic right posterior cerebral artery pressure curve, $A_{p2d}$ is an area of a diastolic right posterior cerebral artery pressure curve, $S_{p1}$ is a blood flow volume of the left posterior cerebral artery, and $S_{p2}$ is a blood flow volume of the right posterior cerebral artery.

The compliances $C_{a1}$ and $C_{a2}$ and the resistances $R_{a1}$ and $R_{a2}$ of the left and right anterior cerebral arteries are calculated by Equation 5 to 8, respectively.

The compliance of the left anterior cerebral artery is $$C_{a1} = \frac{A_{a1S} - A_{a1d}}{P_{a1S} - P_{a1d}} \cdot \frac{S_{a1}}{(A_{a1S} + A_{a1d})(1+K)} \quad \text{Equation 5}$$

The compliance of the right anterior cerebral artery is $$C_{a2} = \frac{A_{a2S} - A_{a2d}}{P_{a2S} - P_{a2d}} \cdot \frac{S_{a2}}{(A_{a2S} + A_{a2d})(1+K)} \quad \text{Equation 6}$$

The resistances of the left anterior cerebral artery is $$R_{a1} = \frac{A_{a1S} + A_{a1d}}{S_{a1}(1+K)} \quad \text{Equation 7}$$

And the resistance of the right anterior cerebral artery is $$R_{a2} = \frac{A_{a2S} + A_{a2d}}{S_{a2}(1+K)} \quad \text{Equation 8}$$

In Equations 5 to 8, $P_{a1s}$ is a systolic blood pressure of the left anterior cerebral artery, $P_{a1d}$ is a diastolic blood pressure of the left anterior cerebral artery, $P_{a2s}$ is a systolic blood pressure of the right anterior cerebral artery, $P_{a2d}$ is a diastolic blood pressure of the right anterior cerebral artery, $A_{a1s}$ is an area of a systolic left anterior cerebral artery pressure curve, $A_{a1d}$ is an area of a diastolic left anterior cerebral artery pressure curve, $A_{a2s}$ is an area of a systolic right anterior cerebral artery pressure curve, $A_{a2d}$ is an area of a diastolic right anterior cerebral artery pressure curve, $S_{a1}$ is a blood flow volume of the left anterior cerebral artery, $S_{a2}$ is a blood flow volume of the right anterior cerebral artery, and K is a clinical coefficient.

The compliances $C_{m1}$ and $C_{m2}$ and the resistances $R_{m1}$ and $R_{m2}$ of the left and right middle cerebral arteries are calculated by Equation 9 to 12, respectively.

The compliance of the left middle cerebral artery is $$C_{a1} = \frac{A_{a1S} - A_{a1d}}{P_{a1S} - P_{a1d}} \cdot \frac{S_{a1}}{(A_{a1S} + A_{a1d})(1+K)} \quad \text{Equation 9}$$

The compliance of the right middle cerebral artery is $$C_{a2} = \frac{A_{a2S} - A_{a2d}}{P_{a2S} - P_{a2d}} \cdot \frac{S_{a2}}{(A_{a2S} + A_{a2d})(1+K)} \quad \text{Equation 10}$$

The resistances of the left middle cerebral artery is $$R_{a1} = \frac{(A_{a1S} + A_{a1d})K}{S_{a1}(1+K)} \quad \text{Equation 11}$$

And the resistance of the right middle cerebral artery is $$R_{a2} = \frac{(A_{a2S} + A_{a2d})K}{S_{a2}(1+K)} \quad \text{Equation 12}$$

In Equations 9 to 12, $P_{m1s}$ is a systolic blood pressure of the left middle cerebral artery, $P_{m1d}$ is a diastolic blood pressure of the left middle cerebral artery, $P_{m2s}$ is a systolic blood pressure of the right middle cerebral artery, $P_{m2d}$ is a diastolic blood pressure of the right middle cerebral artery, $A_{m1s}$ is an area of a systolic left middle cerebral artery pressure curve, $A_{m1d}$ is an area of a diastolic left middle cerebral artery pressure curve, $A_{m2s}$ is an area of a systolic right middle cerebral artery pressure curve, $A_{m2d}$ is an area of a diastolic right middle cerebral artery pressure curve, $S_{m1}$ is a blood flow volume of the left middle cerebral artery, $S_{m2}$ is a blood flow volume of the right middle cerebral artery, and K is a clinical coefficient.

On the other hand, the main processing unit 210 controls the output unit 240 to display the compliance C and the resistance R of each of the cerebrovascular branches calculated in step 3 as a dot on C-R Chart.

It is reasonable that the sectors of C-R chart, as shown in FIG. 8, can be divided to increase the precision according to the various results of clinics. By the exemplary embodiment of clinical result, the sectors can be defined as the followings.

Sector ① is the area diagnosed as the severity of cerebrovascular origin spasm, sector ② is the area starting the implement of blood vessel stenosis, sector ③ is the area of the implement of blood vessel stenosis, sector ④ is the area of cerebral arteriosclerosis and stenosis, sector ⑤ is the area suspected as origin spasm, sector ⑥ is the area of a normal or the implement of spasm, sector ⑦ is the area of a normal, sector ⑧ and ⑩ are the areas diagnosed as a normal or a cerebrovascular spasm according to subjective symptom, sector ⑨ is the area diagnosed as origin spasm, and sector ⑪ is the area suspected as cerebrovascular spasm or a state of taking cerebrovascular vasodilator.

In the followings, the supplementary theories and clinical data are described to support the above mentioned embodiments.

In the present invention, the main processing unit 210 calculates the plural simultaneous equations of blood pressure and blood flow volume using the measured data.

First, the cerebrovascular system must be simplified to calculate for assessing the cerebrovascular state due to the complexity of cerebrovascular system.

Now, the experimental data for analyzing the cerebrovascular system is like Table 1.

TABLE 1

Experiment Results of Compliance and Resistance in Cerebrovascular System

| Artery | Mark | Length [cm] | Diameter [cm] | Resistance | Compliance |
|---|---|---|---|---|---|
| Internal carotid artery (left, right) | c | 2.5 | 0.4-0.6 | 0.15 | 1.07 |
| Basilar artery | b | 3 | 0.4-0.6 | 0.02 | 0.018 |
| Vertebral artery (left, right) | v | 20 | 0.3-0.5 | 0.25 | 0.7 |
| Posterior cerebral artery 1 (left, right) | pl | 2 | 0.3 | 0.04 | 0.007 |
| Posterior cerebral artery 2 (left, right) | p2 | 7 | 0.3 | 0.14 | 0.0025 |
| Posterior cerebral communicating artery | pc | 2 | 0.12 | 0.586 | 0.00012 |
| Anterior cerebral communicating artery | ac | 0.5 | 0.15 | 0.061 | 0.0005 |
| Anterior cerebral artery (1) | a | 2 | 0.25 | 0.0834 | 0.005 |

TABLE 1-continued

Experiment Results of Compliance and Resistance in Cerebrovascular System

| Artery | Mark | Length [cm] | Diameter [cm] | Resistance | Compliance |
|---|---|---|---|---|---|
| Anterior cerebral artery (2) | a | 5 | 0.25 | 0.21 | 0.0125 |
| Middle cerebral artery | m | 7 | 0.35 | 0.076 | 0.0336 |

Peripheral resistance $R_m^* = 2 \times 10^4$, $R_p^* = 2.6 \times 10^4$, $R_a^* = 3.9 \times 10^4$ dyn·S/cm$^3$ As shown in Table 1 and FIG. 4, the cerebrovascular system can be basically consisted of the internal carotid artery, the vertebral artery, the middle cerebral artery, the anterior cerebral artery and the posterior cerebral artery (As shown in Table 1, the compliance is ignored because the values of it are 1/100~1/10000 against those of the other arteries).

From the experiment results as shown in FIG. 4 and Table 1, it is assumed that the cerebrovascular system is consisted of the internal carotid artery branch, the anterior cerebral artery branch, the middle cerebral artery branch, the posterior cerebral artery branch, the vertebral artery branch and the basilar artery branch. So, if Windkesell's model is applied to each of the artery branches and assuming that poly-elastic tube is made by connecting elastic tubes which are analyzed as a blood flow tube, respectively, under the consideration the blood flow property, it is possible to perfectly analyze the cerebrovascular system as shown in FIG. 4.

First, when each elastic tube is connected to the poly-elastic tube, two models are made by considering the property of blood flow.

If Windkesell's model is applied to each of the artery branches and assuming that the poly-elastic tube is made by connecting elastic tubes under consideration the blood flow property, there are two models for configuring the poly-elastic tube. The poly-elastic tube can be configured on the assumption that the internal carotid artery is divided to the anterior cerebral artery and the middle cerebral artery as shown in FIG. 5, or that the internal carotid artery and the middle cerebral artery is one blood vessel branch as one elastic tube.

According to above described, the cerebrovascular system of FIG. 4 can be studied on the assumption that the internal carotid artery 42, the vertebral artery 48, the middle cerebral artery 43, the anterior cerebral artery 4 and the posterior cerebral artery 45 are one blood flow tube, respectively.

To calculate the compliance, the resistance and the elastic coefficient of blood vessel in the equivalent cerebrovascular branches as shown in FIG. 5, the following problems must be solved.

First, because the 18 biodynamic values including the left and right compliances, resistances and elastic coefficients of the anterior cerebral, the middle cerebral and the posterior cerebral artery branches could not determined by 8 curves of the ultrasonic waves and the pulse waves measured at the entrances of the left and right vertebral arteries 48 and the internal carotid artery 42, the cerebrovascular system of FIG. 4 must be simplified by the assumption which is medically reasonable and without the biodynamical conflict.

From the experimental data as shown in Table 1, it is founded that the compliance $C_p$ of the posterior cerebral artery vs. the compliance $C_{pc}$ of the posterior cerebral communicating artery is 25:1 and the compliance $C_a$ of the anterior cerebral artery vs. the compliance $C_{ac}$ of the anterior cerebral communicating artery is 40:1.

Also, the blood flow volumes of $Q_{pc}$ and $Q_{ac}$ are about 1/300 of those of $Q_a$, $Q_p$ and $Q_m$ where C and R are obtained from the cerebrovascular experiment data, $P_1=P_3$ is 103 mmHg as an average blood pressure, and $P_2=P_4$ is 105 mmHg as an average blood pressure.

From the above facts, the anterior cerebral communicating artery and the posterior cerebral communicating artery are assumed as fixed ends.

Therefore, all communicating arteries are ignored and the compliances and the resistances of the artery branches can be determined.

The assumption is medically reasonable. In facts, the cerebral thrombosis is few occurred in and the cerebral hemorrhage is a few occurred in the anterior cerebral communicating artery and the posterior cerebral communicating artery. So, it is possible to diagnose only with the data of blood pressure and blood flow volume but without the data of compliance and resistance.

Form above mentioned, the cerebrovascular system can be studied to be divided from the communicating artery.

First, the problem for analyzing the posterior cerebral artery is described.

The compliances and the resistances of the left and right posterior cerebral arteries are determined on the assumption that each posterior cerebral artery is an elastic tube. The blood flows are determined on the assumption that the posterior cerebral artery is a simple tube. $P_{p1}=P_{p2}$ and $Q_{p1}$ and $Q_{p2}$ are given at the division point where the basilar artery is divided into the left and right posterior cerebral arteries.

The most difficult problem in the determination of the compliance, the blood flow resistance and the blood flow volume of posterior cerebral artery is to determine the blood flow volume $Q_{p1}$ and $Q_{p2}$ of the left and right posterior cerebral arteries when $P_1=P_{p2}$ at the division point of the basilar artery to the left and right posterior cerebral arteries. The vertebral artery is mixed up at the basilar artery and then is divided at the posterior cerebral artery.

To understand the property of blood flow volume which flows from the basilar artery to the left and right posterior cerebral arteries, an experiment was performed and the results showed that the rate of blood flow volumes of the left and right of Kv*vertebral arteries and Kc*internal carotid arteries had high relationship with the rate of blood flow volumes of the left and right of posterior cerebral arteries.

The experimental process was as like as the followings.

To understand the property of blood flow volume which flows from the basilar artery to the left and right posterior cerebral arteries, total 50 men were used as sample.

The average artery pressure was 118 mmHg-132 mmHg, the blood flow volume was 5.2~7.8 ml/s at the entrance of the basilar artery, and total heart beat periods were selected with 541 pieces. The experiment results are given in Table 2.

TABLE 2

Experiment Results of 50 Male Patients

| No | Blood flow volume of basilar artery [ml/s] | $\zeta = S_{P1}/S_{P2}$ | $\eta = S_{V1}*/S_{V2}*$ |
|---|---|---|---|
| 1 | 6.4 | 1.02 | 1.136 |
| 2 | 7.2 | 1.11 | 1.251 |
| 3 | 5.9 | 0.97 | 1.041 |
| 4 | 5.3 | 1.33 | 1.469 |
| 5 | 6.7 | 1.66 | 1.785 |
| 6 | 5.4 | 0.67 | 0.826 |
| 7 | 7.1 | 0.63 | 0.765 |
| 8 | 6.7 | 1.39 | 1.534 |

TABLE 2-continued

Experiment Results of 50 Male Patients

| No | Blood flow volume of basilar artery [ml/s] | $\zeta = S_{P1}/S_{P2}$ | $\eta = S_{V1}*/S_{V2}*$ |
|---|---|---|---|
| 9 | 6.5 | 1.11 | 1.241 |
| 10 | 5.9 | 1.47 | 1.86 |
| 11 | 6.4 | 0.87 | 1.021 |
| 12 | 6.4 | 1.57 | 1.765 |
| 13 | 6.3 | 0.67 | 0.806 |
| 14 | 5.4 | 0.64 | 0.796 |
| 15 | 6.3 | 0.61 | 0.696 |
| 16 | 6.7 | 1.02 | 1.136 |
| ... | ... | ... | ... |
| 50 | 6.8 | 9.63 | 0.698 |

From the above results, the rate $S_{V1}*/S_{V2}*$ of blood flow volumes of the left and right of vertebral arteries and internal carotid arteries shows to have high relationship with the rate $S_{P1}/S_{P2}$ of blood flow volumes of the left and right of posterior cerebral arteries as like as Equations 13 and 14.

$$\zeta = 1.1\eta + 0.031 \qquad \text{Equation 13}$$

$$\gamma_2 = 0.92 \qquad \text{Equation 14}$$

If the above experiment results are theoretically studied, the reason of the relationship between the blood flow volume rate of left and right internal carotid arteries and vertebral arteries and the blood flow volume rate of the left and right posterior cerebral arteries can be described as followings.

The sigma effect occurs at the region where the basilar artery is connected to the posterior cerebral artery. The anterior and posterior inferior cerebellar arteries and the superior cerebellar arteries suck up the blood of the basilar artery as like as a suction point. Also, the blood flow flowing in the internal carotid artery supports the blood flow in the posterior cerebral artery through the posterior cerebral communicating artery. The amount is 30~38% of total blood flow volumes in the posterior cerebral artery. On the other hand, the blood which flows into the brain has a property conserving axisymmetrical big branches due to the pulling force of the fluid-dynamical velocity boundary layer.

By the phenomenon, the amount of blood flow flowing from the vertebral artery through the basilar artery is not same to that of blood flow flowing into the left and the right posterior cerebral arteries.

If $\eta = S_{V1}*/S_{V2}*$ is the rate of the left and right Kv*vertebral artery blood flow volumes and Kc*internal carotid artery blood flow volumes (here, Kv and Kc are the experimental constants of 0.131-0.152 and 0.73-0.82, respectively) and $\zeta = S_{P1}/S_{P2}$ is the rate of the left and right posterior cerebral artery blood flow volumes, Equation 13 is written as like as Equation 15.

$$\zeta = 1.21\eta + 0.11 \qquad \text{Equation 15}$$

Therefore, the blood flow volume of the posterior cerebral artery which is supplied by 80-85% of the blood flow volume of the vertebral artery and filled up with 29-32% from the internal carotid artery can be calculated by Equations 16 and 17.

$$S_{P1} = 1.24(1.21\eta + 0.11)S_{P2} \qquad \text{Equation 16}$$

$$S_{p2} = 1.24(Q_{v1} + Q_{v2})S_{p1} \qquad \text{+Equation 17}$$

Next, at the division point of the left and right posterior cerebral arteries, $P_{p1} = P_{p2}$ is calculated by Equation 18.

$$P_{p1} = P_{p2} \le P_3 - R_{v3}*Q_3 - R_b*Q_b \qquad \text{Equation 18}$$

From Equation 18, $R_{v3}$ and $R_b$ are calculated by Poisenille equation $$R_v = \frac{128\mu}{\pi} \frac{\lambda}{D^4} = 1.63 \frac{\lambda}{D^4} dyn \cdot S/cm^5 \qquad \text{Equation 64}$$

where $\lambda$ is length of artery, D is diameter, and $\mu$ is viscosity of blood. D is calculated from Flank equation in fluid dynamics.

After the calculation of the Q and P, the main processing unit 210 calculates $C_{ps}$, $C_{pd}$, $R_p$ and $R_b$ of the blood vessel. Now, because the left and the right posterior cerebral arteries are branched from the basilar artery, the posterior cerebral artery can be assumed as a single elastic tube with being the posterior cerebral communicating artery as a fixed end (refer to FIG. 5).

On the other hand, because the cerebrovascular system shows spasm and vibration, the modeled equation of the posterior cerebral artery is divided and solved at systole and diastole of blood vessel.

$$C_{ps} \frac{dP}{dt} + \frac{P - P_v}{R_p} = Q_s \qquad \text{Equation 19}$$

$$0 < t \le T_s$$

$$C_{pd} \frac{dP}{dt} + \frac{P - P_v}{R_p} = Q_d \qquad \text{Equation 20}$$

$$T_s < t \le T(Q = Q_s + Q_d)$$

By the experiment results, the compliance of the systolic blood vessel is same to that of the diastolic blood vessel at 170~180 mmHg of the blood pressure. Therefore, $C_{ps} = C_{pd} = C$.

Equations 19 and 20 show the relationship of P, Q, C and R. The calculations of C and R are using the function relationship of area of blood pressure curve P and blood flow volume S instead of adjusting C and R to coincide blood pressure curve P with blood flow volume curve Q.

The reproducible C and R are obtained from the function relationship of the area vs. the area.

When Equations 19 and 20 are integrated, added to, subtracted from and then re-arranged, it is reduced to Equation 21.

$$\frac{A_S + A_d}{A_S - A_d}(P_S - P_d) = \frac{S_V^*}{C} \qquad \text{Equation 21}$$

where $S_v*$ is the blood flow flowing in the posterior cerebral artery at one cycle beat, $P_s$ is the systolic blood pressure, $P_d$ is a diastolic blood pressure, $A_s$ is an area of blood pressure curve P during the systole, $A_d$ is an area of blood pressure curve P during the diastole.

From Equation 21, the compliances $C_{p1}$ and $C_{p2}$ and the resistances $R_{p1}$ and $R_{p2}$ of the left and right posterior cerebral arteries are calculated as the followings.

The compliance of the left posterior cerebral artery is $$C_{p1} = \frac{A_{p1S} - A_{p1d}}{P_{p1S} - P_{p1d}} \cdot \frac{S_{p1}}{A_{p1S} + A_{p1d}} \qquad \text{Equation 1}$$

The compliance of the right posterior cerebral artery is $$C_{p2} = \frac{A_{p2S} - A_{p2d}}{P_{p2S} - P_{p2d}} \cdot \frac{S_{p2}}{A_{p2S} + A_{p2d}} \quad \text{Equation 2}$$

The resistance of the left posterior cerebral artery is $$R_{p1} = \frac{A_{p1S} + A_{p1d}}{S_{p1}} \quad \text{Equation 3}$$

And the resistance of the right posterior cerebral artery is $$R_{p2} = \frac{A_{p1S} + A_{p1d}}{S_{p2}} \quad \text{Equation 4}$$

In Equations 1 to 4, $P_{p1s}$ is a systolic blood pressure of the left posterior cerebral artery, $P_{p1d}$ is a diastolic blood pressure of the left posterior cerebral artery, $P_{p2s}$ is a systolic blood pressure of the right posterior cerebral artery, $P_{p2d}$ is a diastolic blood pressure of the right posterior cerebral artery, $A_{p1s}$ is an area of a systolic left posterior cerebral artery pressure curve, $A_{p1d}$ is an area of a diastolic left posterior cerebral artery pressure curve, $A_{p2s}$ is an area of a systolic right posterior cerebral artery pressure curve, $A_{p2d}$ is an area of a diastolic right posterior cerebral artery pressure curve, $S_{p1}$ is a blood flow volume of the left posterior cerebral artery, and $S_{p2}$ is a blood flow volume of the right posterior cerebral artery.

Next, the organic and functional changes of the cerebrovascular system are understood by solving the problem of fluid elastic body in the elastic tube where the blood flows on the assumption that the posterior cerebral artery is a single tube as an elastic tube where the blood flows (refer to FIG. 5).

The continuity equation and the motion equation of the fluid elastic body in one elastic tube of blood vessel are considered, $$\frac{\partial A}{\partial t} + \frac{\partial AU}{\partial X} = 0 \quad \text{Equation 22}$$

$$\frac{\partial AU}{\partial t} + \frac{\partial AU^2}{\partial t} = -\frac{A}{\rho}\frac{\partial P}{\partial X} - \frac{\tau\omega}{\rho}\frac{2A}{\rho} \quad \text{Equation 23}$$

In Equations 22 and 23, A is an area of blood vessel, U is a velocity of blood flow, and P is a blood pressure.

$$\tau_\omega = \frac{4\mu U}{Y} \quad \text{Equation 24}$$

In Equation 24, Y is radius of blood vessel, μ is viscosity, and $t_w$ is a tangential stress.

$$\frac{\partial A}{\partial t} = \frac{\partial A}{\partial P}\frac{\partial P}{\partial t}, \frac{\frac{\partial H}{\partial t}}{\frac{\partial AH^2}{\partial t}} = 0\left(\frac{a}{F}\right) \quad \text{Equation 25}$$

In Equation 25, F is an average blood flow velocity and, a is an elastic wave propagation velocity.

$$a = \sqrt{\frac{A \cdot dP}{\rho \cdot dA}} \quad \text{Equation 26}$$

If re-arranged with Equations 22 to 26, $$\frac{A}{\rho a^2} \cdot \frac{\partial P}{\partial t} + \frac{\partial Q}{\partial X} = 0 \quad \text{Equation 27}$$

$$\frac{\rho}{A}\frac{\partial Q}{\partial t} = -\frac{\partial P}{\partial X} - \frac{8\mu\pi Q}{A^2} \quad \text{Equation 28}$$

In Equations 27 and 28, P is a blood pressure curve, μ is viscosity, A is a cross-sectional area of blood vessel, and ρ is a density of blood.

Now, in Equation 28, $$\frac{\rho}{A}\frac{\partial Q}{\partial t}$$

is ignored and then Equation 28 is integrated by X $$\frac{A}{\rho a^2}\frac{dP}{dt} + \frac{A^2(P - P_V)}{8\pi\mu_p} = Q_d \quad \text{Equation 29}$$

From Equation 29, Equation 30 is obtained in a single elastic tube.

$$\frac{A}{\rho PWV^2} = C, R = \frac{8\pi\mu}{A^2} \quad \text{Equation 30}$$

As shown in Equation 30, the changes of the cross-sectional area of the cerebrovascular system occur because of the complementary internal pressure by blood pressure change, spasm, contraction, medicine effects, etc in the cerebrovascular system. As shown in the compliance and the resistance of the blood vessel, the compliance and the resistance are severely fluctuated by blood pressure change, spasm, contraction, medicine effects due to the changes of cross-sectional area of the cerebrovascular system.

The elastic coefficient E represents the organic change of the cerebrovascular system because it is related to the elastic wave propagation velocity and not related with blood pressure change, spasm, contraction, medicine effects, etc in the cerebrovascular system.

On the other hand, by Moensu Korteweg, it is given that $PWV = \sqrt{(E/\rho)(h/d)} = a(h/d)$.

So, the elastic coefficient $E = \rho(d/h)PWV^2$.

Therefore, if A is erased in C and R, the arterial stiffness Asc can be obtained from the relationship equations of μ and PWV $$Asc = K_3 \frac{R^{0.25}}{CR}(1 - S) \quad \text{Equation 31}$$

In Equation 31, S=f(PWV) and $K_3$ is a coefficient of clinics.

Next, for applying the indicators of the cerebrovascular property and the blood flow property to the clinics, the volume of blood flow flowing to the internal carotid artery and the vertebral artery must be calculated.

In the present invention, C and R are calculated by substituting the blood flow volume of the vertebral artery obtained by the ultrasonic Doppler into C and R equations expressed with the area of the internal carotid artery pulse wave curve instead of adjusting C and R to coincide the blood flow curve obtained by the ultrasonic Doppler with the pulse wave curve of the internal carotid artery.

This method means that the horizontal plane error, as a weak point, of the ultrasonic Doppler happening in the determination of the cerebrovascular property does not have an effect on calculating C and R.

In other words, because the blood flow volume obtained by the present ultrasonic measurement technology is used to the clinics, if the blood flow volume is measured by the ultrasonic measurement technology, C, R and Asc can be used to the clinics without any problem.

Next, the problem for analyzing the internal carotid artery with neglecting the communicating artery is described.

As the above case, at the branching point of the anterior cerebral artery and the middle cerebra artery, the blood pressure is $P_a = P_m = P$ and the blood flow volumes are $Q_a$ and $P_m$. The systolic compliance is same to the diastolic compliance. When the anterior cerebral artery and the middle cerebra artery are assumed as a single elastic tube, respectively, the elasticity equations can be given as followings.

$$Q_m = C_m \frac{dP_m}{dt} + \frac{P_m - P_v}{R_m} \qquad \text{Equation 32}$$

$$\left(\frac{R_t}{R_a} + 1\right) Q_a = C_a \frac{dP_a}{dt} + \frac{P_a - P_V}{R_a} \qquad \text{Equation 33}$$

$$(Q_m + Q_a) = Q \ (P_m = P_a = P) \qquad \text{Equation 34}$$

Because the resistance $R_2$ of the right artery is $5.9 \times 10^4 \text{dyn} \cdot \text{S/cm}_5$ and the resistance $R_1$ of the left artery is 3400 dyn·S/cm$^5$ the ratio $R_1/R_2 = 0$.

If re-arranged, $$R_1 = \frac{A_{2S} + A_{2d}}{S_C^*} \qquad \text{Equation 35}$$

$$C = \frac{A_{2S} - A_{2d}}{P_{2s} - P_{2d}} \frac{Qc_C}{A_{2S} + A_{2d}} \qquad \text{Equation 36}$$

$$Asc = K_3 \frac{R^{0.25}}{CR}(1-S) \qquad \text{Equation 31}$$

In Equations 31, 35 and 36, R, C and Asc can't be used to the clinics because of the unknown blood flow volume.

So, to obtain R, C and Asc which are applicable to the clinics, $Q_m$ and $Q_a$ must be calculated in the condition of $P_m = P_a$.

To solve this problem, it is to model the carotid artery system on the assumption that the internal carotid artery and the middle cerebral artery are connected as a single tube and that the anterior cerebral artery is branched from the internal artery and the middle cerebral artery branch (refer to FIG. 6).

Now, $C_m$ is the compliance of the middle cerebral artery, $C_a$ is the compliance of the anterior cerebral blood vessel, $R_m$ is the blood flow resistance of the middle cerebral artery, $R_a$ is the blood flow resistance in the circle of Willis of the anterior cerebral artery, $R_t$ is the blood flow resistance in the other region of the anterior cerebral artery, $P_a$, is the blood pressure of the middle cerebral artery, $P_a$ is the blood pressure of the anterior cerebral artery, $Q_m$ is the blood flow volume of the middle cerebral artery, $Q_a$ is the blood flow volume of the anterior cerebral artery, P is the blood pressure at the connecting point of the internal carotid artery and the circle of Willis, and $P_v$ is the blood pressure of vein.

Also, total compliance C of the anterior cerebral artery and the middle cerebral artery is give by:

$$C = \frac{\Delta V}{\Delta p} \qquad \text{Equation 37}$$

Now, from FIG. 6, when first order approximation function of the internal carotid artery is PWV of the middle cerebral artery, the compliance $C_{cm}$ of the internal carotid artery and the middle cerebral artery can be calculated.

So, $$Sm = Cm^*/(P_m^* - Pmd)(Ams + Amd)/Amd \qquad \text{Equation 38}$$

$$Sa = Sc - Sm \qquad \text{Equation 39}$$

$$P_m \leq P_a = P - R_c Q_c \qquad \text{Equation 40}$$

From the above results, the compliances $C_{a1}$ and $C_{a2}$ and the resistances $R_{a1}$ and $R_{a2}$ of the left and right anterior cerebral arteries are calculated by Equations 5 to 8, respectively.

The compliance of the left anterior cerebral artery is $$C_{a1} = \frac{A_{a1S} - A_{a1d}}{P_{a1S} - P_{a1d}} \cdot \frac{S_{a1}}{(A_{a1S} + A_{a1d})(1+K)} \qquad \text{Equation 5}$$

The compliance of the right anterior cerebral artery is $$C_{a2} = \frac{A_{a2S} - A_{a2d}}{P_{a2S} - P_{a2d}} \cdot \frac{S_{a2}}{(A_{a2S} + A_{a2d})(1+K)} \qquad \text{Equation 6}$$

The resistances of the left anterior cerebral artery is $$R_{a1} = \frac{A_{a1S} + A_{a1d}}{S_{a1}(1+K)} \qquad \text{Equation 7}$$

And the resistance of the right anterior cerebral artery is $$R_{a2} = \frac{A_{a2S} + A_{a2d}}{S_{a2}(1+K)} \qquad \text{Equation 8}$$

In Equations 5 to 8, $P_{a1s}$ is $P_{a1s}$ is a systolic blood pressure of the left anterior cerebral artery, $P_{a1d}$ is a diastolic blood pressure of the left anterior cerebral artery, $P_{a2s}$ is a systolic blood pressure of the right anterior cerebral artery, $P_{a2d}$ is a diastolic blood pressure of the right anterior cerebral artery, $A_{a1s}$ is an area of a systolic left anterior cerebral artery pressure curve, $A_{a1d}$ is an area of a diastolic left anterior cerebral artery pressure curve, $A_{a2s}$ is an area of a systolic right anterior cerebral artery pressure curve, $A_{a2d}$ is an area of a diastolic right anterior cerebral artery pressure curve, $S_{a1}$ is a blood flow volume of the left anterior cerebral artery, $S_{a2}$ is a blood flow volume of the right anterior cerebral artery, and K is a clinical coefficient.

Also, the compliances $C_{m1}$ and $C_{m2}$ and the resistances $R_{m1}$ and $R_{m2}$ of the left and right middle cerebral arteries are calculated by Equation 9 to 12, respectively.

The compliance of the left middle cerebral artery is $$C_{a1} = \frac{A_{m1S} - A_{m1d}}{P_{m1S} - P_{m1d}} \cdot \frac{S_{m1}K}{(A_{m1S} + A_{m1d})(1 + K)} \quad \text{Equation 9}$$

The compliance of the right middle cerebral artery is $$C_{m2} = \frac{A_{m2S} - A_{m2d}}{P_{m2S} - P_{m2d}} \cdot \frac{S_{m1}K}{(A_{m2S} + A_{m2d})(1 + K)} \quad \text{Equation 10}$$

The resistances of the left middle cerebral artery is $$R_{m1} = \frac{(A_{m1S} + A_{m1d})K}{S_{m1}(1 + K)} \quad \text{Equation 11}$$

And the resistance of the right middle cerebral artery is $$R_{m2} = \frac{(A_{m2S} + A_{m2d})K}{S_{m2}(1 + K)} \quad \text{Equation 12}$$

In Equations 9 to 12, $P_{m1s}$ is a systolic blood pressure of the left middle cerebral artery, $P_{m1d}$ is a diastolic blood pressure of the left middle cerebral artery, $P_{m2s}$ is a systolic blood pressure of the right middle cerebral artery, $P_{m2d}$ is a diastolic blood pressure of the right middle cerebral artery, $A_{m1s}$ is an area of a systolic left middle cerebral artery pressure curve, $A_{m1d}$ is an area of a diastolic left middle cerebral artery pressure curve, $A_{m2s}$ is an area of a systolic right middle cerebral artery pressure curve, $A_{m2d}$ is an area of a diastolic right middle cerebral artery pressure curve, $S_{m1}$ is a blood flow volume of the left middle cerebral artery, $S_{m2}$ is a blood flow volume of the right middle cerebral artery, and K is a clinical coefficient.

Next, when the blood flow volume of the carotid artery and the vertebral artery and the average blood pressure $\bar{P}$ of the carotid artery are given, the blood pressure and the blood flow volume of each of the blood vessel branches of the cerebrovascular system are calculated.

At this time, the resistance R of each blood vessel is given by the above obtained value.

In clinics, the blood pressure is given by the multiplication of resistance and blood flow volume.

To calculate the blood pressure and the blood flow volume in the main processing unit 210 of the present invention, the simultaneous equations are given as followings.

$$p_1 = R_{C1}Q_{C1} + R_{m1}Q_{M1} \quad \text{Equation 41}$$

$$p_1 = R_{C1}Q_{C1} + R_{PC1}Q_{PC1} + R_{P12}Q_{P12} \quad \text{Equation 42}$$

$$p_1 = R_{C1}Q_{C1} + R_{a11}Q_{a1} + R_{a12}Q_{a12} \quad \text{Equation 43}$$

$$R_{a12}Q_{a12} + R_{ac}Q_{ac} + R_{a22}Q_{a22} = 0 \quad \text{Equation 44}$$

$$p_2 = R_{C2}Q_{C2} + R_{m2}Q_{m2} \quad \text{Equation 45}$$

$$p_2 = R_{C2}Q_{C2} + R_{a21}Q_{a21} + R_{a22}Q_{a22} \quad \text{Equation 46}$$

$$p_3 = R_{V1}Q_{V1} + R_b Q_b + R_{P11}Q_{P11} + R_{P12}Q_{P12} \quad \text{Equation 47}$$

$$p_4 = R_{V2}Q_{V2} + R_b Q_b + R_{P21}Q_{P21} + R_{P22}Q_{P22} \quad \text{Equation 48}$$

$$R_{C1}Q_{C1} + p_{C1} = p_i \quad \text{Equation 49}$$

$$R_{a12}Q_{a12} = p_{a1} \quad \text{Equation 50}$$

$$R_{a22}Q_{a22} = p_{a2} \quad \text{Equation 51}$$

$$R_{C2}Q_{C2} + p_{C2} = p_2 \quad \text{Equation 52}$$

$$R_{v2}Q_{v2} + p_{v2} = p_4 \quad \text{Equation 53}$$

$$R_{v1}Q_{v1} + p_{v1} = p_3 \quad \text{Equation 54}$$

$$R_{p12}Q_{p12} + R_{p11}Q_{p11} - p_{p1} = 0 \quad \text{Equation 55}$$

$$R_{p22}Q_{p23} + R_{p21}Q_{p21} - p_{p2} = 0 \quad \text{Equation 56}$$

$$Q_{m1} + Q_{pc1} + Q_{a1} - Q_{c1} = 0 \quad \text{Equation 57}$$

$$Q_{a12} + Q_{ac} - Q_{a1} = 0 \quad \text{Equation 58}$$

$$Q_{m2} + Q_{pc2} + Q_{ac} - Q_{c2} = 0 \quad \text{Equation 59}$$

$$Q_{a2} + Q_{ac} - Q_{a22} = 0 \quad \text{Equation 60}$$

$$Q_{p12} - Q_{pc1} - Q_{p11} = 0 \quad \text{Equation 61}$$

$$Q_{p22} - Q_{pc1} - Q_{p21} = 0 \quad \text{Equation 62}$$

$$p_2 = R_{C2}Q_{C2} + R_{PC2}Q_{PC2} + R_{P22}Q_{P22} \quad \text{Equation 63}$$

In the above equations, the unknowns are $Q_{p11}$, $Q_{p12}$, $Q_{p21}$, $Q_{p22}$, $Q_{a11}$, $Q_{a12}$, $Q_{a21}$, $Q_{a22}$, $Q_{m1}$, $Q_{m2}$, $Q_{pc1}$, $Q_{pc2}$, $Q_{ac}$, $P_{a1}$, $P_{a2}$, $P_{c1}$, $P_{c2}$, $P_{v1}$, $P_{v2}$, $P_{p1}$, $P_{p2}$, $P_3$, $P_4$ and $R_b$.

Therefore, if $P_1$, $P_2$, $Q_{v1}$, $Q_{v2}$, $Q_{c1}$ and $Q_{c2}$ are known, the above simultaneous equations can be solved.

Because the present invention enables to early diagnose the risk of cerebrovascular diseases by analyzing an elastic coefficient for observing the organic change of each cerebrovascular branch and by calculating a cerebrovascular blood flow volume, a cerebrovascular compliance, and a cerebrovascular resistance for observing blood flow properties of a cerebrovascular system and the organic and the functional changes of each cerebrovascular branch, the cerebrovascular analyzer of the present invention has a very high industrial applicability.

The invention claimed is:

1. A cerebrovascular analyzer, comprising:
a bio-signal measurement system including a bio-signal measuring sensor unit that comprises an electrocardiogram (ECG) sensor, a phonocardiogram (PCG) sensor, an accelerated plethysmogram (APG) sensor and an ultrasonic sensor, and a bio-signal reception and process unit that is connected to each of the sensors of the bio-signal measuring sensor unit for receiving and processing bio-signals measured by the sensors; and
an analysis indicator calculation system including a main processing unit that is connected to the bio-signal reception and process unit for communicating and calculating biodynamic indicators of a cerebrovascular system from the bio-signals, an input unit that is connected to the main processing unit for receiving control commands of a user, and an output unit that is connected to the main processing unit for displaying the calculated results,
wherein the APG sensor is a cuff pulse wave sensor, a carotid artery pulse wave sensor or a femoral artery pulse wave sensor;
wherein the bio-signal measurement system is configured to obtain an ECG waveform, a PCG waveform and an APG waveform synchronously by the bio-signal measuring sensor unit;
wherein the main processing unit is programmed to calculate the biodynamic indicators from basic data including a cerebrovascular pressure curve synthesized with the bio-signals of the bio-signal measurement system, a systolic area and a diastolic area of the cerebrovascular pressure curve and a cerebrovascular blood flow volume;

wherein the main processing unit is programmed to carry out the steps of:

(1) receiving basic information data from the input unit and receiving the bio-signals from the bio-signal measurement system;

(2) analyzing waveforms from the bio-signals and obtaining the cerebrovascular pressure curve, the systolic area and the diastolic area of the cerebrovascular pressure curve and the cerebrovascular blood flow volume from the waveforms; and (3) calculating the biodynamic indicators from the cerebrovascular pressure curve, the areas of the cerebrovascular pressure curve, the cerebrovascular blood flow volume and the basic information data and displaying the results of cerebrovascular analysis;

wherein the cerebrovascular system comprises a left posterior cerebral artery and a right posterior cerebral artery; and wherein step 3 further comprises calculating compliances $C_{p1}$ and $C_{p2}$ and resistances $R_{p1}$ and $R_{p2}$ of the left and right posterior cerebral arteries using the following equations:

the compliance of the left posterior cerebral artery is $$C_{p1} = \frac{A_{p1s} - A_{p1d}}{P_{p1s} - P_{p1d}} \cdot \frac{S_{p1}}{A_{p1s} + A_{p1d}},$$

the compliance of the right posterior cerebral artery is $$C_{p2} = \frac{A_{p2s} - A_{p2d}}{P_{p2s} - P_{p2d}} \cdot \frac{S_{p2}}{A_{p2s} + A_{p2d}},$$

the resistance of the left posterior cerebral artery is $$R_{p1} = \frac{A_{p1s} + A_{p1d}}{S_{p1}},$$

and the resistance of the right posterior cerebral artery is $$R_{p2} = \frac{A_{p1s} + A_{p1d}}{S_{p2}}$$

where $P_{p1s}$ is a systolic blood pressure of the left posterior cerebral artery, $P_{p1d}$ is a diastolic blood pressure of the left posterior cerebral artery, $P_{p2s}$ is a systolic blood pressure of the right posterior cerebral artery, $P_{p2d}$ is a diastolic blood pressure of the right posterior cerebral artery, $A_{p1s}$ is an area of a systolic left posterior cerebral artery pressure curve, $A_{p1d}$ is an area of a diastolic left posterior cerebral artery pressure curve, $A_{p2s}$ is an area of a systolic right posterior cerebral artery pressure curve, $A_{p2d}$ is an area of a diastolic right posterior cerebral artery pressure curve, $S_{p1}$ is a blood flow volume of the left posterior cerebral artery, and $S_{p2}$ is a blood flow volume of the right posterior cerebral artery.

2. The cerebrovascular analyzer of claim 1, wherein the main processing unit is programmed to control the output unit display the cerebrovascular compliance $C_{p1}$ and the cerebrovascular resistance $R_{p1}$ of the left posterior cerebral artery as a dot on a Compliance-Resistance (C-R) chart and to display the cerebrovascular compliance $C_{p2}$ and the cerebrovascular resistance $R_{p2}$ of the right posterior cerebral artery as another dot on the Compliance-Resistance (C-R) chart.

3. A cerebrovascular analyzer, comprising:

a bio-signal measurement system including a bio-signal measuring sensor unit that comprises an electrocardiogram (ECG) sensor, a phonocardiogram (PCG) sensor, an accelerated plethysmogram (APG) sensor and an ultrasonic sensor, and a bio-signal reception and process unit that is connected to each of the sensors of the bio-signal measuring sensor unit for receiving and processing bio-signals measured by the sensors; and an analysis indicator calculation system including a main processing unit that is connected to the bio-signal reception and process unit for communicating and calculating biodynamic indicators of a cerebrovascular system from the bio-signals, an input unit that is connected to the main processing unit for receiving control commands of a user, and an output unit that is connected to the main processing unit for displaying the calculated results, wherein the APG sensor is a cuff pulse wave sensor, a carotid artery pulse wave sensor or a femoral artery pulse wave sensor;

wherein the bio-signal measurement system is configured to obtain an ECG waveform, a PCG waveform and an APG waveform synchronously by the bio-signal measuring sensor unit;

wherein the main processing unit is programmed to calculate the biodynamic indicators from basic data including a cerebrovascular pressure curve synthesized with the bio-signals of the bio-signal measurement system, a systolic area and a diastolic area of the cerebrovascular pressure curve and a cerebrovascular blood flow volume;

wherein the main processing unit is programmed to carry out the steps of:

(1) receiving basic information data from the input unit and receiving the bio-signals from the bio-signal measurement system;

(2) analyzing waveforms from the bio-signals and obtaining the cerebrovascular pressure curve, the systolic area and the diastolic area of the cerebrovascular pressure curve and the cerebrovascular blood flow volume from the waveforms; and (3) calculating the biodynamic indicators from the cerebrovascular pressure curve, the areas of the cerebrovascular pressure curve, the cerebrovascular blood flow volume and the basic information data and displaying the results of cerebrovascular analysis;

wherein the cerebrovascular system comprises a left anterior cerebral artery and a right anterior cerebral artery; and wherein step 3 further comprises calculating compliances $C_{a1}$ and $C_{a2}$ and resistances $R_{a1}$ and $R_{a2}$ of the left and right anterior cerebral arteries using the following equations:

the compliance of the left anterior cerebral artery is $$C_{a1} = \frac{A_{a1s} - A_{a1d}}{P_{a1s} - P_{a1d}} \cdot \frac{S_{a1}}{(A_{a1s} + A_{a1d})(1 + K)},$$

the compliance of the right anterior cerebral artery is $$C_{a2} = \frac{A_{a2S} - A_{a2d}}{P_{a2S} - P_{a2d}} \cdot \frac{S_{a2}}{(A_{a2S} + A_{a2d})(1 + K)},$$

the resistances of the left anterior cerebral artery is $$R_{a1} = \frac{A_{a1S} + A_{a1d}}{S_{a1}(1 + K)},$$

and
the resistance of the right anterior cerebral artery is $$R_{a2} = \frac{A_{a2S} + A_{a2d}}{S_{a2}(1 + K)}$$

where $P_{a1s}$ is a systolic blood pressure of the left anterior cerebral artery, $P_{a1d}$ is a diastolic blood pressure of the left anterior cerebral artery, $P_{a2s}$ is a systolic blood pressure of the right anterior cerebral artery, $P_{a2d}$ is a diastolic blood pressure of the right anterior cerebral artery, $A_{a1s}$ is an area of a systolic left anterior cerebral artery pressure curve, $A_{a1d}$ is an area of a diastolic left anterior cerebral artery pressure curve, $A_{a2s}$ is an area of a systolic right anterior cerebral artery pressure curve, $A_{a2d}$ is an area of a diastolic right anterior cerebral artery pressure curve, $S_{a1}$ is a blood flow volume of the left anterior cerebral artery, $S_{a2}$ is a blood flow volume of the right anterior cerebral artery, and K is a clinical coefficient.

4. The cerebrovascular analyzer of claim 3, wherein the main processing unit is programmed to control the output unit to display the cerebrovascular compliance $C_{p1}$ and the cerebrovascular resistance $R_{a1}$ of the left anterior cerebral artery as a dot on a Compliance-Resistance (C-R) chart and to display the cerebrovascular compliance $C_{p2}$ and the cerebrovascular resistance $R_{p2}$ of the right anterior cerebral artery as another dot on the Compliance-Resistance (C-R) chart.

5. A cerebrovascular analyzer, comprising:
a bio-signal measurement system including a bio-signal measuring sensor unit that comprises an electrocardiogram (ECG) sensor, a phonocardiogram (PCG) sensor, an accelerated plethysmogram (APG) sensor and an ultrasonic sensor, and a bio-signal reception and process unit that is connected to each of the sensors of the bio-signal measuring sensor unit for receiving and processing bio-signals measured by the sensors; and
an analysis indicator calculation system including a main processing unit that is connected to the bio-signal reception and process unit for communicating and calculating biodynamic indicators of a cerebrovascular system from the bio-signals, an input unit that is connected to the main processing unit for receiving control commands of a user, and an output unit that is connected to the main processing unit for displaying the calculated results,
wherein the APG sensor is a cuff pulse wave sensor, a carotid artery pulse wave sensor or a femoral artery pulse wave sensor;
wherein the bio-signal measurement system is configured to obtain an ECG waveform, a PCG waveform and an APG waveform synchronously by the bio-signal measuring sensor unit;
wherein the main processing unit is programmed to calculate the biodynamic indicators from basic data including a cerebrovascular pressure curve synthesized with the bio-signals of the bio-signal measurement system, a systolic area and a diastolic area of the cerebrovascular pressure curve and a cerebrovascular blood flow volume;
wherein the main processing unit is programmed to carry out the steps of:
(1) receiving basic information data from the input unit and receiving the bio-signals from the bio-signal measurement system;
(2) analyzing waveforms from the bio-signals and obtaining the cerebrovascular pressure curve, the systolic area and the diastolic area of the cerebrovascular pressure curve and the cerebrovascular blood flow volume from the waveforms; and
(3) calculating the biodynamic indicators from the cerebrovascular pressure curve, the areas of the cerebrovascular pressure curve, the cerebrovascular blood flow volume and the basic information data and displaying the results of cerebrovascular analysis;
wherein the cerebrovascular system comprises a left middle cerebral artery and a right middle cerebral artery; and
wherein step 3 further comprises calculating compliances $C_{m1}$ and $C_{m2}$ and resistances $R_{m1}$ and $R_{m2}$ of the left and right middle cerebral arteries using the following equations:
the compliance of the left middle cerebral artery is $$C_{m1} = \frac{A_{m1S} - A_{m1d}}{P_{m1S} - P_{m1d}} \cdot \frac{S_{m1}K}{(A_{m1S} + A_{m1d})(1 + K)},$$

the compliance of the right middle cerebral artery is $$C_{a2} = \frac{A_{m2S} - A_{m2d}}{P_{m2S} - P_{m2d}} \cdot \frac{S_{m2}K}{(A_{m2S} + A_{m2d})(1 + K)},$$

the resistance of the left middle cerebral artery is $R_{m1}= (A_{m1s}+A_{m1d})K/(S_{a1}(1+K))$ to $R_{m1}=(A_{m1s}+A_{m1d})K/(S_{m1}(1+K))$, and
the resistance of the right middle cerebral artery is $R_{m2}= (A_{m2s}+A_{m2d})K/(S_{a2}(1+K))$ to $R_{m2}=(A_{m2s}+A_{m2d})K/(S_{m2}(1+K))$
where $P_{m1s}$ is a systolic blood pressure of the left middle cerebral artery, $P_{m1d}$ is a diastolic blood pressure of the left middle cerebral artery, $P_{m2S}$ is a systolic blood pressure of the right middle cerebral artery, $P_{m2d}$ is a diastolic blood pressure of the right middle cerebral artery, $A_{m1s}$ is an area of a systolic left middle cerebral artery pressure curve, $A_{m1d}$ is an area of a diastolic left middle cerebral artery pressure curve, $A_{m2S}$ is an area of a systolic right middle cerebral artery pressure curve, $A_{m2d}$ is an area of a diastolic right middle cerebral artery pressure curve, $S_{m1}$ is a blood flow volume of the left middle cerebral artery, $S_{m2}$ is a blood flow volume of the right middle cerebral artery, and K is a clinical coefficient.

6. The cerebrovascular analyzer of claim 5, wherein the main processing unit is programmed to control the output unit to display the cerebrovascular compliance $C_{m1}$ and the cerebrovascular resistance $R_{m1}$ of the left middle cerebral artery as a dot on a Compliance-Resistance (C-R) chart and to display the cerebrovascular lar compliance $C_{m2}$ and the cerebrovascular resistance $R_{m2}$ of the right middle cerebral artery as another dot on the Compliance-Resistance (C-R) chart.

* * * * *